US012773185B2

(12) United States Patent
Vincent et al.

(10) Patent No.: US 12,773,185 B2
(45) Date of Patent: Oct. 27, 2026

(54) ULTRASOUND PROBE AND METHOD FOR IMPLEMENTING SAME

(71) Applicant: Echopen Factory, Paris (FR)

(72) Inventors: Benoit Vincent, Paris (FR); Clement Le Couedic, Puteaux (FR); Jerome Dubois, Orleans (FR)

(73) Assignee: Echopen Factory, Paris (FR)

( * ) Notice: Subject to any disclaimer, the term of this patent is extended or adjusted under 35 U.S.C. 154(b) by 134 days.

(21) Appl. No.: 18/563,989

(22) PCT Filed: May 25, 2022

(86) PCT No.: PCT/FR2022/000051
§ 371 (c)(1),
(2) Date: Oct. 7, 2024

(87) PCT Pub. No.: WO2022/248777
PCT Pub. Date: Dec. 1, 2022

(65) Prior Publication Data

US 2025/0032091 A1 Jan. 30, 2025

(30) Foreign Application Priority Data

May 26, 2021 (FR) ....................................... 2105473

(51) Int. Cl.
*A61B 8/00* (2006.01)

(52) U.S. Cl.
CPC .......... *A61B 8/4461* (2013.01); *A61B 8/4427* (2013.01); *A61B 8/54* (2013.01)

(58) Field of Classification Search
CPC ....... A61B 8/4461; A61B 8/4427; A61B 8/54; A61B 8/5207
See application file for complete search history.

(56) References Cited

U.S. PATENT DOCUMENTS

| | | | |
|---|---|---|---|
| 4,149,419 A | 4/1979 | Connel, Jr. et al. | |
| 4,276,491 A | 6/1981 | Daniel | |
| 4,418,698 A | 12/1983 | Dory | |
| 4,773,268 A | 9/1988 | Inbar et al. | |

(Continued)

FOREIGN PATENT DOCUMENTS

| | | | |
|---|---|---|---|
| CN | 106571758 | 4/2017 | |
| CN | 106571758 A * | 4/2017 | ................ H02P 8/38 |

(Continued)

OTHER PUBLICATIONS

International Search Report dated Aug. 10, 2022, issued in PCT Application No. PCT/FR2022/000051, filed May 25, 2022.

*Primary Examiner* — Kaitlyn E Sebastian
(74) *Attorney, Agent, or Firm* — Workman Nydegger

(57) ABSTRACT

This implementation method is used for an ultrasound scanner including an ultrasound scanner probe used to explore an area of interest on the human body, in which a drive system including a stepper motor and a carrier supporting a transducer element is controlled in order to pick up echo lines via the transducer element. An imaging algorithm is applied and image points are analyzed along an arc at a given depth for two series of successive emission and return echo lines, in order to determine the angular offset of the image points in the two successive arcs and calculate the angular offset of the emission echo lines and return lines induced by the operation of the drive system, and then offset is corrected.

19 Claims, 3 Drawing Sheets

(56) References Cited

U.S. PATENT DOCUMENTS

| | | | | |
|---|---|---|---|---|
| 5,740,804 | A * | 4/1998 | Cerofolini ............ | A61B 8/4461 73/633 |
| 6,645,151 | B2 | 11/2003 | Irloka et al. | |
| 7,635,335 | B2 | 12/2009 | Hwang et al. | |
| 10,349,893 | B2 | 7/2019 | Lee et al. | |
| 2003/0055338 | A1 | 3/2003 | Steininger et al. | |
| 2007/0016060 | A1 * | 1/2007 | Hwang ................ | A61B 8/4494 600/459 |
| 2009/0030326 | A1 * | 1/2009 | Kim ..................... | A61B 5/1075 600/459 |
| 2010/0324416 | A1 | 12/2010 | Burbank et al. | |
| 2010/0324418 | A1 * | 12/2010 | El-Aklouk ............ | G01S 7/5208 600/459 |
| 2020/0323592 | A1 | 10/2020 | Ferrara | |

FOREIGN PATENT DOCUMENTS

| | | | |
|---|---|---|---|
| CN | 109951129 | A | 6/2019 |
| EP | 0 045 265 | A1 | 7/1981 |
| EP | 0 079 284 | A1 | 5/1983 |
| EP | 0 201 137 | A1 | 5/1986 |
| EP | 0 476 495 | A1 | 3/1992 |
| EP | 1 744 178 | A2 | 11/2005 |
| FR | 2 409 742 | A1 | 6/1979 |
| FR | 2 479 531 | A1 | 10/1981 |
| FR | 2516246 | A1 | 5/1983 |
| FR | 2516249 | A1 | 5/1983 |
| WO | 2006/078456 | A1 | 7/2006 |
| WO | 2017/009735 | A1 | 1/2017 |
| WO | 2019/122665 | A1 | 6/2019 |

* cited by examiner

ULTRASOUND PROBE AND METHOD FOR IMPLEMENTING SAME

TECHNICAL AREA

The invention relates to the general field of ultrasonography, and more particularly to ultrasonographic probes comprising at least one piezoelectric transducer element with an oscillating & pivoting mount, with mechanical sectorial scanning functions. More specifically, some aspects of the invention relate to the precision of the transducer element's position. The invention applies not only to the probes, but also to ultrasound scanners with embedded probes, and implementation methods.

STATE OF THE ART

Professionals are aware that ultrasound scanners comprise an ultrasound emission and reception probe, designed to be placed on part of the body (in particular the human body) corresponding to the area of interest to be explored, and a central electronic system powered by a processor that applies algorithms, using a keyboard, display and visualization, adjustment and storage means, etc., to form an image from the echoes received by the probe following the ultrasound emissions. Such ultrasound scanners are used in a number of medical applications, including, but not limited to, cardiology and obstetrics, to acquire information for study, research, monitoring and diagnosis purposes. For sedentary use, the central system is typically mounted on a mobile cart and connected to the operating probe by cables. Such central systems are bulky and heavy, limiting the applications. For semi-nomadic use, portable ultrasound scanners, similar to laptop computers, were considered. Even lighter ultrasound scanners were then proposed for nomadic use in any location (e.g. U.S. Pat. No. 10,349,893, WO 2017009735), in which case the probe is controlled via wireless communication with a smartphone (i.e. a portable digital device able to run an application suitable for certain functions, not necessarily a phone, but also potentially a tablet or other device).

Professionals are aware that ultrasound probes are contained in a case used to handle and protect contents, with an external format suitable for the purpose, and housing at least one single or multiple piezoelectric transducer elements facing an acoustic window. Such transducers usually operate at a resonant frequency between 1 MHz and 30 MHz. It may be necessary to place a coupling fluid between the transducer element(s) and the acoustic window, particularly with mechanically-scanned probes. The transducer element transmits an ultrasound detection signal to an area of interest on the body for which an ultrasound image is required, which could be described as an ultrasound beam in a certain median direction. The transducer element picks up the echoes reflected by the impacted body tissues, interfaces or organs in the area of interest. The operator moves the probe relative to the body at different locations and angles to investigate the target organs. Such ultrasound probes may also include powering, processing, adjusting, controlling, monitoring, connecting and communicating components, etc.

Professionals are aware that the frequency must be adapted to the depth of the target area of interest, therefore either a broadband transducer element supporting several frequencies is provided, or several transducers corresponding to specific frequencies (e.g. U.S. Pat. No. 4,276,491), or several different low-band probes connected to the system.

The probe can be unidirectional or multidirectional depending on requirements and design, with sectorial scanning of the target area of interest. Although such scanning is mainly electronic, mechanical scanning is also feasible (e.g. FR 2516246, EP 0045265, EP 0079284). Depending on the set-up used, several transducer elements are secured, spaced on a pivoting mount (e.g. disc, wheel or drum), which is mechanically driven by a motor with oscillating and pivoting axes and possibly an intermediate motion transmission system (e.g. belt, pinions or connecting rod). The active transducer scans the sectors in the area facing the scanning zone.

When scanning alternating sectors, the transducer emits an ultrasound pulse towards the area to be scanned at each successive position, and in return picks up a line of echoes returned by the medium. The transducer picks up a set of around one hundred echo lines for each complete swept sector covering approximately 40° to 90°. The area of interest is visually reconstructed by juxtaposing these echo lines using an imaging algorithm. The successive to-and-fro scans swept several times per second produce an animated model of the area of interest.

Professionals are also aware that the drive motor for a transducer element can be a stepper motor (e.g. U.S. Pat. No. 7,635,335, EP 0476495), with inherent advantages such as simplicity, robustness, low cost, reliability, high torque at a low speed, and suitability for the environment of an ultrasound probe (EP 1744178). However, professionals are also aware that stepper motors bring the inevitable problem of angular offset between the actual position of the transducer element and its theoretical position (EP 0079284), caused by the angular inaccuracy of the motor and the inaccuracy induced by the motion transmission system, particularly during use. This angular inaccuracy, however slight, distorts the final image and/or the superposition of emitted and return images, which adversely affects the quality of the rendering. As a result, electronic scanning may be preferable to mechanical scanning, but the benefits of the latter are lost.

According to US 2003/0055338, while the probe comprises a stepper motor, a closed-loop optical servo device is installed to detect the position of the array of transducer elements. According to U.S. Pat. No. 4,773,268, the drum supporting the multiple transducer elements on the mount and the motor outlet pinion, itself fitted with a position encoder, are especially designed to prevent the slippage of the connecting belt. Either one or more encoders may be used indifferently (e.g. FR 2516246, EP 1838753, U.S. Pat. No. 6,645,151 with two encoders). FR 2409742 provides for additional optical equipment to generate signals indicating the position of the rotary transducer element and subsequently transmit signals to a servo controller. EP 0201137 provides for an optical encoder. According to FR 2479531, offsets arise between scans, therefore digital processing and a storage device are required.

CN109951129 describes a method for controlling a stepper motor, without a position sensor, comprising the following steps: observe the estimated position of the motor rotor at the target time as a function of the two-phase current and the two-phase voltage of the motor; compare the theoretical position of the motor rotor with the estimated position at the target time to determine compensation for position error for the motor rotor; compensate the position of the motor rotor based on position error. CN106571758 describes a stepper motor offset compensation method used for an ultrasound probe which is also equipped with a transducer. The method involves the following steps: acquire actual transducer position information by calculating the number of motor steps required for the transducer to reach its actual position; compare the actual position with the target position to obtain stepper motor offset data; compare the desynchronization data with a predefined threshold to determine within which threshold range the desynchronization data fall; determine the appropriate compensation mode for the desynchronization data as a function of the threshold range; compensate the data. With this set-up, the motor is used to compensate for the pre-calculated offset.

Furthermore, WO2019122665 describes a method used to determine the deployed position of an implantable medical device based on a three-dimensional image of an area of interest comprising the vascular structure in which a positioning point has been defined, including several steps: determine an artery centerline, place the device in an initial position with respect to the centerline, and simulate the final position of the device based on the loads applied by the walls of the vascular structure. With this set-up, the centerline is determined by placing points at different longitudinal positions along the vascular structure in order to minimize fluid travel time along said points between a point of entry into the vascular structure and a point of exit from the vascular structure, and travel time is minimized using a gradient descent algorithm. These points form the centerline.

SUMMARY

Ultrasound scanners are required for mobile use, and more specifically embedded probes, which can be used for a wide range of purposes (in particular, working at several depths to observe different areas of interest), particularly in emergency situations. These scanners must be able to guide diagnostics, particularly in emergency situations, must be simple, lightweight and robust by design, reliable for the intended purpose, provide a simple, robust and effective means of reconstructing images for the practitioner's intended purpose, be cost-effective (in terms of manufacturing, use and maintenance), and be compatible with a standard smartphone, as carried by the operator. The smartphone must be able to both control the probe and receive, display, save and transmit the images obtained, using a specialist application if necessary, and provide an image of a suitable quality for the intended purpose, which will particularly help to compensate, to some extent, the image distortions caused by the very design of the probe.

In particular, an ultrasound probe with mechanical sectorial scanning is required, comprising a stepper motor and a motion transmission system, which reduces, more specifically minimizing and eliminating or almost eliminating, image shaking due to the offset between successive images. In particular, it is essential to reduce, more specifically minimize and eliminate or almost eliminate such image shaking, without any need for additional measuring equipment for errors caused by defects affecting mechanical parts of the probe.

To this end, with reference to an initial aspect, an implementation method is proposed for an ultrasound scanner comprising an ultrasound probe for exploring an area of interest on the human body, in which:

- a drive system including a stepper motor and a transducer element carrier is controlled mechanically, scanning alternating sectors from a reference position, and
- the transducer element is used to pick up several echo lines after receiving multiple successive ultrasound pulses emitted towards the area of interest, controlled by a firing and movement scheduling pilot,
- an imaging algorithm is run to visually reconstruct the area of interest by juxtaposing the echo line image points, and an animated model of the area of interest is produced based on successive to-and-fro scans.

The process:

- the image points are analyzed along an arc at a given depth of the area of interest, with two series of successive emitted and return echo lines, to determine the angular offset of the image points between the two successive emitted and return arcs and calculate the angular offset between the emitted echo lines and the return echo lines, associated with the operation of the drive system, and
- the offset is corrected by approximating the successive emitted and return images, in particular by superimposing or almost superimposing the images, incorporating the calculated offset associated with the operation of the drive system, in order to reduce, more specifically minimize and eliminate or almost eliminate, image shaking for the final image.

A stepper motor without an encoder is used in one set-up.

With this method, the effects of the defects affecting the mechanical probe equipment on the final image are harnessed and used to directly correct the image, so that these effects (image shaking) are reduced, more specifically minimized and eliminated or almost eliminated, without any need to use additional error measuring equipment.

According to one set-up, in order to measure the offset:

- the series of echo lines for the emitted image is acquired and the curve of an emission arc reconstructed, comprising all the image points in the echo lines located at the same depth,
- the series of echo lines for the return image is acquired and the curve of a return arc reconstructed, comprising all the image points in the echo lines located at the same depth,
- a gradient descent algorithm is used to minimize the distance between the points on the emission arc curve and the return arc curve by progressively offsetting one with respect to the other, until the offset giving the minimum distance is achieved, as the angular offset between the emission and return echo lines.

According to another set-up, in order to measure the offset:

- a gradient descent algorithm is applied to an initial emission arc and an initial return arc to obtain an initial offset d1,
- a gradient descent algorithm is then applied to the initial return arc and a subsequent second emission arc to obtain a second offset d2,
- and the final offset for mechanical play is defined as (d1−d2)/2.

According to a first set-up, in order to correct the offset, the angular offset is repeatedly calculated and, when the offset calculated in this way is considered to be reliable, the images returned to the imaging algorithm are corrected by applying an inverse rotation to the offset calculated in this way and considered to be reliable.

According to a second set-up, to correct the offset, the angular offset is repeatedly calculated, and when the calculated offset is considered to be reliable, it is permanently saved and the firing and movement scheduling pilot is instructed to time-shift the emissions with respect to the return movement, as a function of the reliable calculated offset.

According to one option offered by the invention, with this process, on the one hand, probe movement is sensed, and on the other hand:

if the first step is to identify a target area of interest, the probe is moved across large areas in order to search for a location, in which case the probe is in nominal fast frame rate mode and the image obtained has nominal resolution, and if, in a second phase, the target area of interest has been identified and a higher-resolution image is required, the probe is kept static or quasi-static, and can then be set to a slower frame rate and the image obtained has a higher resolution.

According to one set-up:

a carrier is installed with n transducer elements, each with its own frequency, n frequencies are chosen to obtain n examination depths, the frequency corresponding to the required examination depth is selected, and the stepper motor is instructed to move the carrier and bring the transducer element corresponding to the selected frequency to its operating position.

According to one set-up, n is equal to three, and the frequencies are equal to or close to 3.5 MHz, 5 MHz and 7.5 MHz respectively.

According to one set-up:

a portable digital device is provided, able to run an application suitable for the execution of a functionality, such as a smartphone or a tablet, with communications capabilities such as Wi-Fi or Bluetooth protocol or Internet protocol, a screen, a control device and memory, an ultrasound probe with communications capabilities is provided, and the portable digital device and the probe are set up to communicate with each other, the portable digital device is used to parameterize and control the probe, display the images obtained by and received from the probe on the screen of the portable digital device, and transmit the images obtained by and received from the probe to an external storage platform.

Depending on the set-up used, the angular offset of the lines associated with the operation of the drive system is calculated from either the portable digital device or the probe; and/or the angular offset thus calculated is compensated from either the portable digital device or the probe.

According to a second aspect, an ultrasound scanner suitable for implementation using the method described is proposed, comprising:

an ultrasound probe for exploring an area of interest on the human body, comprising a drive system including a stepper motor and a carrier supporting a mechanically-driven transducer element, which scans alternating sectors from a reference position, the transducer element which is able to pick up several echo lines when receiving multiple successive ultrasound pulses emitted towards the zone of interest, controlled by a firing and movement scheduling pilot an imaging algorithm is used to visually reconstruct the area of interest by juxtaposing the echo line image points, and an animated model of the area of interest is produced based on successive to-and-fro sweeps, means of analyzing the image points along an arc at a given depth of the area of interest, with two series of successive emission and return echo lines, to determine the angular offset of the image points between the two successive emission and return arcs and calculate the angular offset between the emission echo lines and the return echo lines, associated with the operation of the drive system, and a means of correcting the offset by approximation, particularly best approximation, primarily by superimposing or almost superimposing the emission and successive return images, incorporating the calculated offset associated with the operation of the drive system, which reduces, minimizes and, more specifically, eliminates or almost eliminates image shaking.

According to one feature, the stepper motor has no encoder.

According to one set-up, the carrier supports n transducer elements, each with its own frequency, to allow for n examination depths, and a control system is adapted to instruct the stepper motor to move the carrier and bring the transducer element corresponding to the selected frequency to its operating position.

According to one set-up, n is equal to three, and the frequencies are equal to or close to 3.5 MHz, 5 MHz and 7.5 MHz respectively.

According to one set-up, the ultrasound scanner:

also comprises a portable digital device, able to run an application suitable for the execution of a functionality, such as a smartphone or a tablet, with communications capabilities such as Wi-Fi or Bluetooth protocol or Internet protocol, a screen, a control device and memory, the probe has the communication capabilities to link to the portable digital device, the portable digital device is arranged to be able to parameterize and control the probe, display the images obtained by and received from the probe on the screen of the portable digital device, and transmit the images obtained by and received from the probe to an external storage platform.

According to one set-up, the probe in the ultrasound scanner comprises:

a wet compartment containing a coupling liquid and provided with an acoustic window, housing the transducer element carrier such as a rotating drum, a dry compartment housing electronic equipment, communications resources and a power supply unit, as well as ports for a battery charger and a computer.

Either the wet compartment only houses the transducer element (rotary drum) and the rest of the drive system, including the stepper motor, is housed in the dry compartment, with a dynamic seal (e.g. on the shaft) separating the two compartments, or the entire drive unit, transducer carrier (rotary drum) and the rest of the drive unit (including the stepper motor) is housed in the wet compartment, in which case no dynamic seal is required to separate the two compartments, and the electrical connections to the stepper motor are sealed.

According to one set-up, the drive system for the ultrasound scanner includes a motion transmission system between the stepper motor and the transducer element carrier, such as a toothed belt interlocking with notches on a rotary pinion at the stepper motor outlet and the notches on a rotary pinion at the transducer element carrier inlet.

According to the set-up, the portable digital device and the probe are arranged to ensure that:

the resources of the portable digital device are used to calculate the angular offset of the lines associated with the operation of the drive system and/or the compensation of the angular offset thus calculated; and/or probe resources are used to calculate the angular offset of the lines associated with the operation of the drive system and/or compensation of the angular offset thus calculated.

DESCRIPTION OF SET-UPS

Figure 1:
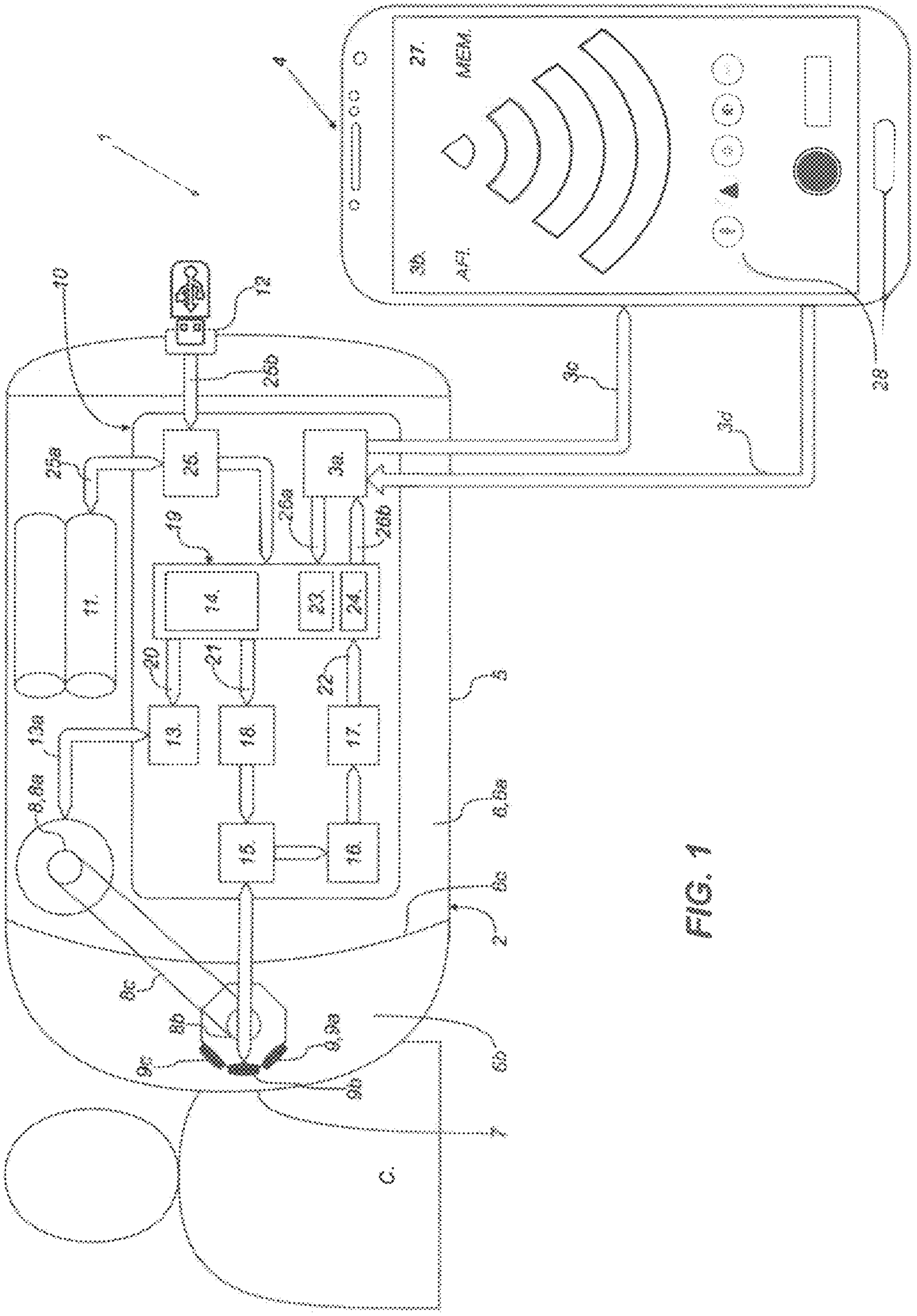
FIG. 1 is a schematic view illustrating an ultrasound scanner according to the invention, comprising an ultrasound probe for exploring an area of interest on the human body, with a drive system including a stepper motor and a carrier supporting a transducer element, operating equipment, means of communication with a portable digital device and the digital device in question.
Figure 2:
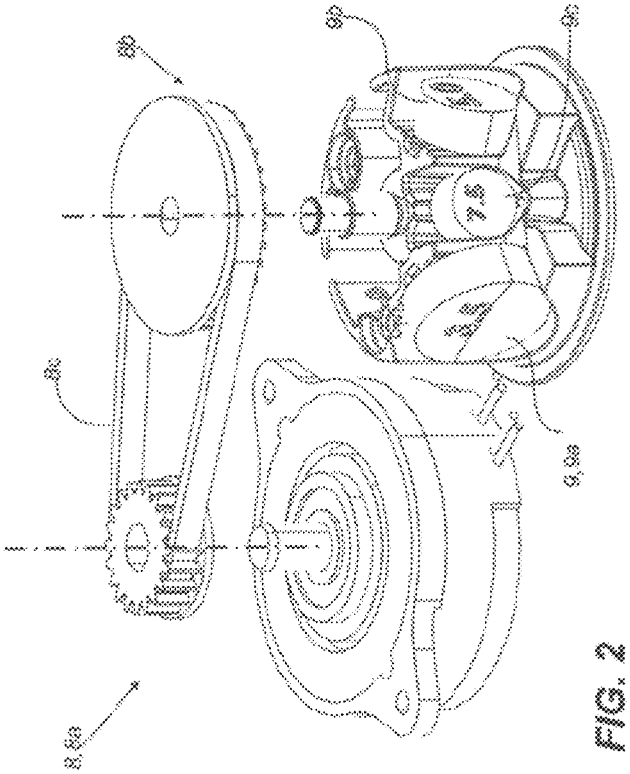
FIG. 2 is a schematic view of the drive system including a stepper motor, a transducer element carrier, a motion transmission system between the stepper motor and the transducer element carrier.

The following description refers to the drawings shown in the figures. The terms used are to be understood and interpreted in light of the scope of the invention and the state of the art presented above.

The invention presents two aspects, on the one hand, an ultrasound scanner 1 and, on the other hand, implementation resources for such an ultrasound scanner 1, comprising an ultrasound probe 2 for exploring an area of interest ZI on the human body C, comprising equipment 3*a* for communication with a separate computer. In the set-up under consideration, the computer is a portable digital device 4, capable of running an application suitable for the execution of a functionality, such as a smartphone or tablet, and with communications capabilities 3*b*. Once communications capabilities 3*a* and 3*b* are installed to communicate with each other, they can particularly operate via the WI-FI or Bluetooth protocol or the Internet protocol. This specific arrangement ensures that probe 2 is portable.

As professionals are well aware, probe 2 has a rigid, outer casing 5, with an ergonomic shape for easy handling by the operator. For example, this shape bulges towards the two ends and narrows in the middle to form a manual grip. Housing 5 features a removable cover providing access to an inner housing space 6, comprising a dry compartment 6*a* where the cover is located, and a wet compartment 6*b* located at the opposite end and forming a contact zone 7 with a human body contact zone C for exploring the area of interest ZI. The two compartments 6*a* and 6*b* are separated from each other by a watertight partition 6*c*.

In the specific set-up shown in schematic view FIG. 1, dry compartment 6*a* houses part 8*a* of drive system 8 of at least one transducer element 9, the electronic equipment 10 of probe 2, including communications capability 3*a* and power supply unit 11. It also comprises one or more ports 12, such as ports for a battery charger, computer or other peripheral device.

In this same specific set-up (FIG. 1), the wet compartment 6*b* has an ultrasound-transparent acoustic window designed to come into contact with the human body contact zone C, and contains an ultrasound beam transmission coupling fluid. Wet compartment 6*b* also contains at least one transducer element 9, which is mobile thanks to drive system part 8*b*.

Part 8*a* of drive system 8 for one transducer element 9 housed in dry compartment 6*a* comprises a stepper motor which, according to one feature, is not equipped with an encoder unlike many conventional professional set-ups. One pilot 13 is associated with stepper motor 8*a*. Drive system part 8*b* housed in the wet compartment 6*b* comprises a fixed carrier for transducer element 9, such as a drum 8*b*, which can rotate thanks to stepper motor 8*a*, via a motion transmission system 8*c*, such as a toothed belt interlocking with the notches of a rotating pinion at the outlet of stepper motor 8*a* and the notches of a rotating pinion at the inlet of drum 8*b*. Such gears are used to minimize the angular offset caused by the movement of stepper motor 8*a* and drum 8*b*, which cannot, however, be completely eliminated on a permanent basis.

In the specific set-up (FIG. 1), in which wet compartment 6*b* only houses drum 8*b*, while stepper motor 8*a* is housed in dry compartment 6*a*, a dynamic seal (e.g. on the shaft) is provided for leaktight partition 6*c* between the two compartments 6*a* and 6*b* (shown as a symbol in drawing FIG. 1 with the motion transmission system 8*c* passing through leaktight partition 6*c*).

The specific set-up shown in schematic view FIG. 1 does not exclude another, unshown, set-up, in which both drum 8*b* and stepper motor 8*a*, which is not equipped with an encoder, are housed in wet compartment 6*b*, in which case the dynamic seal previously provided is no longer necessary, as the electrical connections to the stepper motor are designed to be watertight.

Stepper motor 8*a* is instructed to mechanically drive drum 8*b* to scan alternating sectors from a reference position, at a sweep angle between 40° and 90° which can be adjusted if required. In addition, transducer element 9 is able to emit ultrasound pulses towards the area of interest ZI corresponding to several successive firing operations, controlled by one firing and movement scheduling pilot 14 in probe 2. Transducer element 9 is also able to pick up several emission echo lines (LEA), return echo lines (LER) when receiving the pulses. This arrangement ensures that transducer element 9 is brought to the reference position facing the acoustic window by stepper motor 8*a*, and is then rotated by stepper motor 8*a*, over a certain distance in one direction and then in the other, to scan both emissions and echoes. The axis of transducer element 9 continues to face the acoustic window. The scan of emission echoes is symbolized in FIG. 3 by the arrow FA, while the return scan is symbolized by the arrow FR. As shown, transducer element 9 is controlled by pilot 14, which schedules movements and firing, with emission lines spaced at a constant angular pitch generating return echo lines. These successive emission lines are symbolized in FIG. 3 by LEA lines (solid lines), while the successive return echo lines are symbolized in this figure by LER lines (dotted lines). As professionals are well aware, the emissions pass through the various parts of the human body towards the area of interest ZI, and, as a function of the frequency of transducer element 9—which correlates with the depth P of the area of interest ZI in the human body C—, the echo lines LEA and LER are used by imaging systems to produce images with different gray levels depending on the organs or tissues passed through by the emission lines, to visually reconstruct the area of interest ZI by juxtaposing the image points in the echo lines and an animated model of the area of interest is produced based on the successive to-and-fro scans. The operating method used for probe 2 therefore ensures that drive system 8, including stepper motor 8*a*, drum 8*b* and transmission system 8*c*, is instructed to mechanically drive transducer element 9 to scan alternating sectors from a reference position. This method is deployed so that transducer element 9 picks up several echo lines LEA and LER when receiving several successive ultrasound pulses emitted towards the area of interest ZI, as instructed by firing and movement scheduling pilot 14. The operating method used for probe 2 therefore ensures that an image formation algorithm (AFI) is implemented to visually reconstruct the area of interest ZI by juxtaposing the image points in echo lines LEA, LER and an animated model of the area of interest ZI is produced based on the successive to-and-fro scans.

According to a specific, but non-limiting set-up, drum 8*b* supports n transducer elements 9, each with its own frequency, allowing for n examination depths P of the area of interest ZI. Frequency can be adjusted on the fly between series of images. Pilot 13 for stepper motor 8*a* can be controlled for this purpose from smartphone 4, instructing stepper motor 8*a* to move drum 8*b* in order to bring transducer element 9 corresponding to the selected frequency to the reference position. This arrangement allows different depths P to be explored with the same probe 2, without any need for several probes or to replace these probes. This specific arrangement is particularly flexible and versatile thanks to the portable design of probe 2 made possible by combining probe 2 with smartphone 4 to form ultrasound scanner 2. For example, in one set-up, n is equal to three, and the frequencies are equal or close to 3.5 MHz, 5 MHz and 7.5 MHz respectively. If ultrasound scanner 1 thus comprises three transducer elements 9*a*, 9*b*, 9*c*, the latter are arranged on drum 8*b* with angular spacing designed to minimize the total angular excursion of drum 8*b* between the most distant transducer elements (e.g. 9*a* and 9*b* according to FIGS. 1 and 3). The invention is not exclusive to this set-up and may feature a different number of transducer elements. For example, with n transducer elements 9, the procedure for operating probe 2 is as follows: drum 8*b* contains n transducer elements, each with its own frequency; the n frequencies are chosen to allow for n examination depths P; the frequency corresponding to the required examination depth P is selected and the stepper motor is instructed to move drum 8*b* and bring transducer element 9 corresponding to the selected frequency to its reference position.

Dry compartment 6*a* contains electronic unit 10 for probe 2 in addition to stepper motor 8*a*, and, if applicable, power supply unit 11, and at least one and generally several ports 12. This electronic unit comprises:

- pilot 13 for stepper motor 8*a*, combined with stepper motor 8*a* via functional link 13*a*,
- a transducer element switch 15, combined with transducer elements 9,
- combined with switch 15, an output line for transducer elements 9, including analog amplifier 16 and analog-to-digital converter 17,
- combined with switch 15, an input line for transducer element(s) 9, including high-voltage pulse generator 18,
- digital core 19 with control link 20 to pilot 13 for stepper motor 8*a*, control link 21 to high-voltage pulse generator 18, and link 22 supplied with data from analog-to-digital converter 17; digital core 19 including firing and movement scheduling pilot 14, state machine 23 and detection module 24 for the envelope of the digitized raw high-frequency signal,
- power supply management module 25, combined with power supply unit 11 at 25*a* and port 12 used to connect a charger at 25*b*,
- communications capabilities 3*a* are bidirectional: output at 26*a* for commands sent to digital core 19 and input at 26*b* for line envelopes sent to smartphone 4.

Smartphone 4, or equivalent, can run an application suitable for the execution of a functionality, i.e. software or an application which can apply the AFI imaging algorithm to visually reconstruct the area of interest ZI by juxtaposing the image points in the echo lines LEA and LER and an animated model of the area of interest ZI is produced based on the successive to-and-fro scans of transducer element 9. In addition, as professionals are generally aware, smartphone 4, or equivalent, also includes, in particular, screen 27, control device 28, MEM memory, and one or more ports. Smartphone 4, or equivalent, is designed to be able to parameterize and control probe 2. In addition, smartphone 4, or equivalent, is designed to be able to apply the AFI imaging algorithm. Finally, smartphone 4, or equivalent, is primarily configured to display the images obtained by and received from probe 2 on screen 27, and transmit the images obtained by and received from probe 2 to an external storage platform. Schematic view FIG. 1 shows the functional connection running from probe 2 to smartphone 4, or equivalent, as a symbol denoted 3*c*, while the functional connection running from probe 2 to smartphone 4, or equivalent, is shown as a symbol denoted 3*d*.

According to plans, ultrasound scanner 1 will be capable of analyzing the image points along an arc at a given depth P of the area of interest ZI for two series of successive emission LEA and return LER echo lines, in order to determine the angular offset of the image points in the two successive arcs AA and AR (FIG. 3) and calculate the angular offset of the emission lines LEA and return echo lines LER. This angular offset is associated with the operation of drive system 8. This analysis is based on a comparison of the location of the image points corresponding to the same depth P of the area of interest ZI for two successive series of echo lines LEA and LER. In fact, while ideally—in the absence of any induced deviation, for example, by mechanical drive system 8, and providing that the area observed does not move—the corresponding image points for two series of lines LEA and LER should be superimposed, in practice, this is not the case, causing the image to shake.

In order to reduce, more specifically minimize and eliminate or almost eliminate, this image shaking, the plan is to analyze the image points, using the indicated resources, in order to determine the angular offset of the image points in the emission LEA and return LER echo lines, and to calculate the angular offset for these echo lines LEA and LER, and subsequently to correct offset as a function of the calculated angular offset, using an offset corrector. The operating procedure for probe 2 therefore ensures that the image points along an arc AA and AR are analyzed, at a given depth P of the area of interest ZI for two series of successive emission echo lines LEA and return echo lines LER, to determine the angular offset of the image points for the two successive arcs and calculate the angular offset of the emission echo lines and return echo lines. This offset is associated with the operation of drive system 8. The offset is then corrected by approximating the successive emission and return images, particularly by superimposing or almost superimposing the images, incorporating the calculated offset for the operation of drive system 8. In this way, the effects caused by defects affecting the mechanical drive system 8 for probe 2 on the final image are harnessed and used to directly correct the image, so that the effects of the defects affecting the mechanical drive system 8, i.e. image shaking, are reduced, more specifically minimized and eliminated or almost eliminated, without any need to use additional error measuring equipment.

Figure 3:
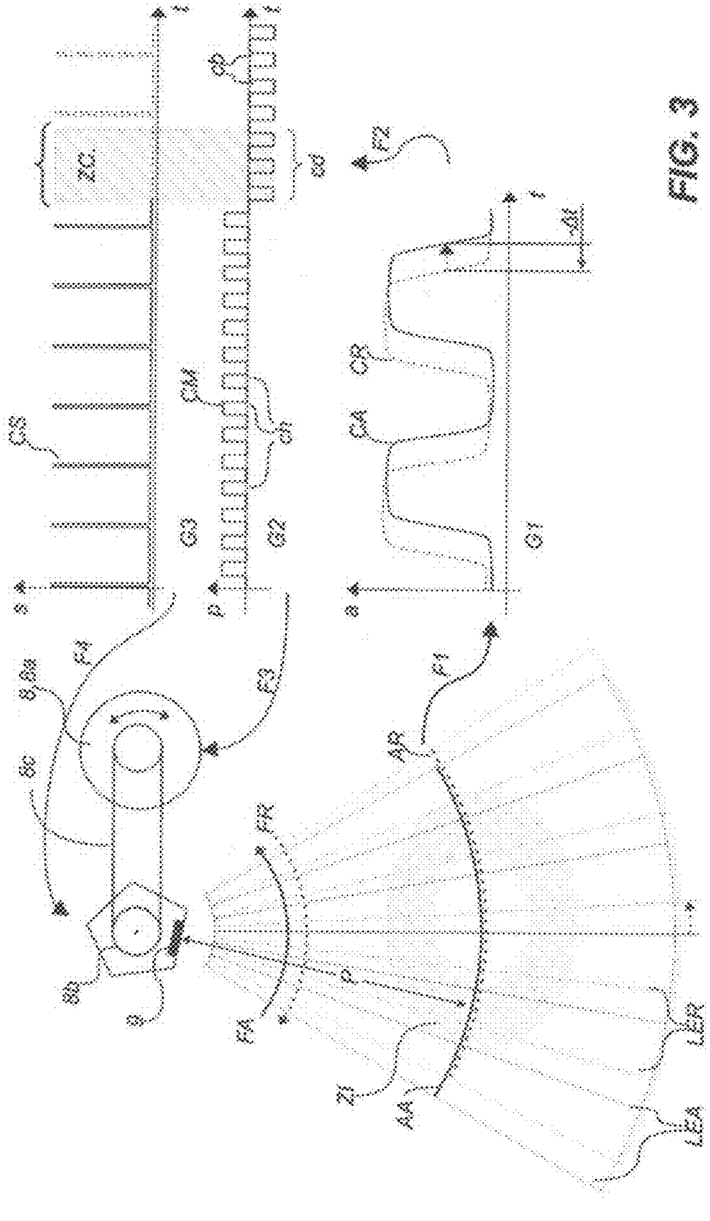
FIG. 3 is a schematic diagram illustrating the implementation of the correction loop for angular offset between the emission and return echo lines, combined with the operation of the ultrasound probe drive system.

The process is symbolically illustrated in FIG. 3. Stepper motor 8*a*, drum 8*b*, transmission system 8*c*, transducer element 9, chosen for implementation purposes, and located in the reference position, and the successive emission echo lines LEA (solid line) and the successive return echo lines LER (dashed line) obtained by analyzing the source pulses (not shown), emission arc AA and return arc AR at the given depth P of the area of interest ZI are shown in the left-hand part of the diagram.

The lower right-hand part of FIG. 3 features a G1 graph, with time t on the x-axis, indicated in proportion to the angle of the emitted pulses due to the constant angular velocity of the drive system in this part of the scan, and echo amplitude a on the y-axis. This graph shows the two curves CA-emission curve-(solid line) and CR-return curve-(dashed line) with variation in echo amplitude as a function of time for the two arcs AA and AR respectively located at a depth P, reconstructed from two series of successive emission LEA and return LER echo lines. FIG. 3 shows that the two curves CA and CR, which have similar shapes and amplitude corresponding to exploration at the same depth P in the absence of movement, are not superimposed, but offset from each other along the x-axis (time). In this case, the return curve CR is shifted by $-\Delta t$ in relation to emission curve CA. This graph G1 illustrates how angular offset is calculated, and must then be compensated for (graphs G2 and G3).

The upper right-hand part of FIG. 3 features two graphs G2 and G3 (arranged above G2), with time t on the common x-axis and the steps p of stepper motor 8*a* on the y-axis (reflecting the corresponding control of stepper motor 8*a* by scheduler 14 amplified by pilot 13) for graph G2 (bottom) and, for graph G3 (top), the pulses s emitted by transducer element 9. On graph G2, the CM curve comprises a series of positive segments ch corresponding to the steps of stepper motor 8*a* for the emission sweep and then (with respect to time t), negative segments cb for the return sweep. In order to correct the measured offset (in relation to the offset shown in graph G1), after the series of positive segments ch and before the series of negative segments cb, a series of negative offset compensation segments cd-shown in a compensation zone ZC, hatched—is added to the CM curve. The number of segments corresponds to the offset shown in graph G1. The greater the offset, the greater the number of offset compensation segments cd, and conversely the smaller the offset. In graph G3, the CS curve comprises a series of peaks at constant time intervals, related to the operation of stepper motor 8*a*, illustrating firing. In the compensation zone ZC, the CS curve has no peaks, reflecting the fact that no firing was triggered during the corresponding time period. These graphs G2 and G3 illustrate potential offset corrections.

The arrows F1, F2, F3 and F4 in FIG. 3 illustrate, in this set-up, the firing servo loop as a function of the offset associated with the operation of drive system 8 for probe 2. Arrow F1 is directed towards graph G1 and symbolizes offset for echo lines LEA and LER, as a result of firing, and due to the mechanical problems affecting drive system 8. Arrow F2, between graph G1 and graphs G2 and G3, symbolizes the offset for stepper motor 8*a* and firing. Arrow F3 between graph G2 and stepper motor 8*a* symbolizes stepper motor 8*a* control for offset corrections. Arrow F4 between graphic G3 and transducer element 9 symbolizes firing control for offset corrections.

FIG. 3 illustrates that the effects caused by the defects affecting the mechanical drive system for probe 2 on the final image are directly harnessed and used to correct the image, reducing the effects caused by the defects affecting the mechanical drive system (image shaking), more specifically minimizing and eliminating or almost eliminating these effects, without any need for additional error measuring equipment.

One possible way to measure the offset is described below. The following procedure may be used in an optimal situation in which the imaged area of interest ZI is high-contrast and stationary relative to the tip of probe 2:

- the series of echo lines LEA for the emission image is acquired and the curve CA of an emission arc AA is reconstructed, consisting of all the image points in the echo lines LEA located at the same depth P,
- the series of LER echo lines of the return image is acquired and the curve CR of a return arc AR is reconstructed, consisting of all the image points in the LER echo lines located at the same depth P,
- we attempt to minimize the distance between the points on the curve CA of the emission arc AA and the curve CB of the return arc AR, using a gradient descent algorithm, by gradually offsetting one with respect to the other.
- the minimum distance offset is taken to be the angular offset between the LEA emission echo lines and the LER return echo lines.

By implementing a gradient descent algorithm and minimizing the distance between the points on the emission arc curve AA and the return arc curve AR, it may not be possible to perfectly superimpose or almost perfectly superimpose the emission images and the successive return images, but they can be approximated in all events (compared to a situation where the invention process is not implemented), and in particular they will be subject to best approximation, i.e. to the extent of the minimization obtained. For this reason, if we fail to eliminate or almost eliminate the shaking in the final image, we will reduce it, and more specifically minimize it, to ensure that the image is acceptable to a practitioner.

This situation may not be optimal as described above, because the area of interest imaged has high contrast, and is moving uniformly perpendicular to the tip of probe 2, and not stationary. Indeed, most of the time, practitioners move the ultrasound probe 2 to search for the area of interest ZI, and this movement introduces additional offset in successive images which must not be taken into account, as it is simply the consequence of moving ultrasound probe 2, and is not linked to the mechanical play previously discussed and which we aim to correct. In this case, the gradient descent algorithm can be successively applied to an emission arc and a return arc to obtain an initial offset d1, and then to this same return arc and the subsequent emission arc to obtain a second offset d2. If dj is the systematic offset associated with mechanical play and dm the offset associated with probe 2 movement, we obtain:

$$d1 = dj + dm$$

$$d2 = -dj + dm$$

-continued and therefore $dj = (d1 - d2)/2$ and $dm = (d1 + d2)/2$.

It may be that the situation is neither optimal as described above nor even sub-optimal as just mentioned, because the area of interest imaged has low contrast or the motion is not uniform and perpendicular to the tip of probe 2. In this case, several optional strategies can be adopted to improve results. One potential strategy is to randomly vary the depth P of the measurement arc to increase the chances of analyzing a higher-contrast area of interest ZI. Another potential strategy is to take around 10 images per second, allowing about 10 offsets per second to be evaluated. Given that the damage caused by the mechanical play to be corrected is mainly constant or changing very slowly, primarily as a function of wear or thermal variations, a high number of offset values can be measured and a correction only applied if a clear trend emerges, for example never more than one correction per hour or per day.

Several possible, but non-limiting, offset correction methods are now described. According to a first set-up, offset is corrected by repeatedly calculating angular offset, then, when the offset calculated in this way is considered to be reliable, correcting the return images produced by the AFI imaging algorithm by applying an inverse rotation of the offset calculated in this way and considered to be reliable. The term "reliable offset" means that repetitive calculations of the offset lead to values with a low degree of variation, as the degree of variation can be adjusted at the discretion of the probe 2 manufacturer according to the required level of performance. This initial set-up provides a sort of instant remedial correction.

Considering a second set-up, designed for future preventive corrections, as described previously, angular offset is repeatedly calculated until the calculated offset is considered to be reliable, particularly if a new probe is first used after assembly. However, once this offset has been saved on a permanent basis, firing and movement scheduling pilot 14 is instructed to time-shift emissions as a function of return movements, and according to the offset thus calculated and considered to be reliable. This second set-up is shown in FIG. 3, simulating a low-defect mechanism, ensuring that the emission and return images are superimposed. The new offset calculations for the image will generally give zero results, apart from slow offset caused by wear and tear on the mechanism, which will regularly be compensated for and saved once the amplitude of this offset exceeds a threshold deemed by the manufacturer of probe 2 to excessively impact image quality.

The method and the ultrasound scanner 1 described for the invention are compatible with another operating procedure if practitioners move probe 2, and subsequently stabilize the probe in relation to an area of interest ZI, given that the relative displacement of probe 2 over the area of interest ZI can be determined using the algorithm implemented or by any other means, such as, for example, a movement sensor associated with probe 2. Indeed, if probe 2 is moving, practitioners generally aim to obtain a fluid image with a fast refresh rate (e.g. 10 frames per second) and normal spatial resolution. On the other hand, if probe 2 is stabilized in an area of interest ZI, practitioners generally prefer a high-resolution image, to the detriment of the refresh rate. With this approach, the return lines are deliberately and temporarily offset by a ½ step to ensure that they fit exactly between the emission lines. This artificially doubles the number of lines in an image, but at half the refresh rate (e.g. 5 frames per second). The image reconstruction algorithm adapts to this new arrangement of emission and return echo lines. The angular offset measurement algorithm also adapts to this new arrangement in order to continue detecting probe movements. If the algorithm detects probe movement again, it switches back to fast refresh/normal resolution mode. Thus, thanks to this option offered by the invention, with the process, on the one hand, probe 2 movement is detected, and on the other hand:

- if the first step is to identify a target area of interest, the probe is moved across large areas for the purpose of finding locations, the probe is then set to nominal fast frame rate mode and the image obtained has nominal resolution, and
- if, in a second phase, the target area of interest has been identified and a higher-resolution image is required, the probe is kept static or quasi-static, the probe can then be set to a slower frame rate and the image obtained has a higher resolution.

Depending on the set-up, probe 2 movement is detected by either the algorithm or a movement sensor integrated in probe 2.

Several set-up variants are possible for calculating the angular offset of the lines associated with the operation of the drive system, and for compensating the angular offset calculated in this way. For example, the angular offset can be calculated using either portable digital device 4 or probe 2 and, alternatively or cumulatively, the calculated angular offset can be compensated from either portable digital device 4 or probe 2. Consequently, portable digital device 4 and probe 2 are arranged accordingly, so that:

- portable digital device resources are used to calculate the angular offset of the lines associated with the operation of the drive system and/or the compensation of the angular offset thus calculated; and/or
- probe resources are used to calculate the angular offset of the lines associated with the operation of the drive system and/or the compensation of the angular offset thus calculated.

The invention claimed is:

1. A method for operating an ultrasound scanner comprising an ultrasound probe for exploring an area of interest on a human body, the method comprising:

- controlling a mechanical drive system including a stepper motor, a motion transmission system, and a carrier supporting a transducer element fitted on a rotating mount via the stepper motor;
- acquiring, by the transducer element, emission echo lines by scanning one direction and return echo lines by scanning another direction opposite the one direction when receiving several successive ultrasound pulses emitted towards the area of interest, controlled by a firing and movement scheduling controller;
- analyzing image points of the emission echo lines and image points of the return echo lines along emission and return echo arcs, respectively, at a given depth of the area of interest to determine an angular offset between the image points in two successive emission and return arcs caused by defects affecting the mechanical drive system;
- correcting the angular offset by approximating two successive emission and return images by superimposing the two successive emission and return images, and incorporating the determined angular offset associated with an operation of the mechanical drive system; and visually reconstructing, by an imaging algorithm, the area of interest by juxtaposing the image points along the emission echo lines and the return echo lines and producing an animated model of the area of interest based on successive scans around the one and another directions and based on the corrected angular offset, wherein the transducer element, fixed to the carrier, is mechanically driven by the stepper motor and scans alternating sectors from a reference position, and wherein the defects affecting the mechanical drive system are addressed on a final image by reducing image shaking caused by the angular offset between successive images, associated with operation and initial motion of the mechanical drive system.

2. The method according to claim 1, wherein a stepper motor without an encoder is used.

3. The method according to claim 1, wherein, to measure the angular offset:

the series of the emission echo lines for the emission image are acquired and a curve of an emission arc is reconstructed, the emission image including all image points in the echo lines located at a same depth, the series of the return echo lines of the return image are acquired and a curve of a return arc is reconstructed, the return image including all image points in the return echo lines located at a same depth, and a gradient descent algorithm is applied to minimize a distance between the image points on the curve of the emission arc and the image points on the curve of the return arc by progressively offsetting each curve with respect to the other until the angular offset giving a minimum distance is retained as the angular offset between the emission and return echo lines.

4. The method according to claim 1, wherein, to measure the angular offset:

a gradient descent algorithm is applied to an initial emission arc and an initial return arc to obtain an initial offset d1, a gradient descent algorithm is applied to the initial return arc and a subsequent second emission arc, to obtain a second offset d2, and the angular offset caused by mechanical effects is defined as (d1−d2)/2.

5. The method according to claim 1, wherein, in order to correct the angular offset, the angular offset is repeatedly calculated, and when an offset value calculated is considered to be reliable, the return images are corrected by applying an inverse rotation of the calculated angular offset and considered to be reliable.

6. The method according to claim 1, wherein, in order to correct the angular offset, the angular offset is repeatedly calculated, and when an offset value calculated is considered to be reliable, it is saved on a permanent basis and the firing and movement scheduling controller is instructed to time-shift firing with respect to the return movement, as a function of the calculated angular offset and considered to be reliable.

7. The method according to claim 1, wherein, a probe movement is sensed, and:

if, in a first phase, a target area of interest is to be identified, the probe is moved across a large area in order to identify a location set to a nominal fast frame rate mode, and the final image has a first resolution, and if, in a second phase, the target area of interest has been identified and a higher resolution image is required, the probe is kept static or quasi-static, the probe is set to a slower frame rate, and the higher resolution image has a higher resolution than the first resolution.

8. The method according to claim 1, wherein the carrier supports n transducer elements, each with a respective frequency, wherein n frequencies are chosen to allow for n examination depths, wherein a frequency corresponding to a required examination depth is selected, and wherein the stepper motor is instructed to move the carrier and bring each transducer element corresponding to the selected frequency to a respective reference position.

9. The method according to claim 8, wherein n is equal to three, and the frequencies are equal to 3.5 MHz, 5 MHz, and 7.5 MHz, respectively.

10. The method according to claim 1, wherein the ultrasound scanner further comprises:

a portable digital device capable of executing a functionality with communications capabilities, a screen, a control device, and a memory, and wherein a probe is provided for exploring an area of interest on the human body and comprises a resource configured to analyze image points along an arc at a given depth, such that the angular offset between the emission echo lines and the return echo lines is determined and caused by defects affecting the mechanical drive system, the probe being fitted with a processor configured to correct the angular offset, and communications capabilities and the portable digital device, and the probe being configured to communicate with each other, and wherein the portable digital device is used to parameterize and control the probe, display the images obtained by and received from the probe on the screen of the portable digital device, and transmit the images to an external storage platform.

11. The method according to claim 10, wherein the angular offset between the emission and return echo lines associated with the operation of the mechanical drive system is calculated using either the portable digital device or the probe, and/or wherein the calculated angular offset is compensated from either the portable digital device or the probe.

12. An ultrasound scanner comprising:

a probe for exploring an area of interest on a human body, comprising a mechanical drive system including a stepper motor, a motion transmission system, and a carrier for a transducer element secured on the carrier to be mechanically driven in a scan alternating between sectors from a reference position, wherein the transducer element is configured to pick up emission echo lines for an emission image by scanning one direction and return echo lines for a return image by scanning another direction opposite the one direction when receiving successive ultrasound pulses, which have been emitted towards and reflected from the area of interest, controlled by a firing and movement scheduling controller, wherein the area of interest is visually reconstructed by juxtaposing image points along the emission echo lines and the return echo lines, and an animated model of the area of interest is produced based on successive scans the one and another directions, wherein an angular offset between the emission echo lines and the return echo lines is determined based on defects affecting the mechanical drive system, wherein a processor is configured to analyze the image points of emission and return echo lines along emission and return echo arcs, respectively, at a given depth of the area of interest for two series of successive emission and return echo lines, in order to determine the angular offset of the image points in the two successive emission and return arcs and calculate the angular offset of the two successive emission and return echo lines, associated with an operation of the mechanical drive system, and wherein the processor is further configured to correct the angular offset by image approximation, and by superimposing the successive emission images and the successive return images, and by incorporating the calculated angular offset associated with the operation of the mechanical drive systems, and wherein the defects affecting the mechanical drive system are addressed on a final image by reducing image shaking caused by the angular offset between successive emission and return images, associated with the operation and initial motion of the mechanical drive system.

13. The ultrasound scanner according to claim 12, wherein the stepper motor is not fitted with an encoder.

14. The ultrasound scanner according to claim 12, wherein the carrier supports n transducer elements, each with a respective frequency to allow for n examination depths, and wherein a control device is configured to control the stepper motor to move the carrier and bring each transducer element corresponding to the respective frequency to a respective reference position.

15. The ultrasound scanner according to claim 14, wherein n is equal to three, and wherein the frequencies are equal to or close to 3.5 MHz, 5 MHz, and 7.5 MHz, respectively.

16. The ultrasound scanner according to claim 12, further comprising a portable digital device capable of executing a functionality with communications capabilities, a screen, a control device, and a memory, wherein the probe with communications capabilities is further configured to communicate with the communications capabilities of the portable digital device, and wherein the portable digital device is configured to parameterize and control the probe, display the images obtained by and received from the probe on the screen of the portable digital device, and transmit the images to an external storage platform.

17. The ultrasound scanner according to claim 12, wherein the probe comprises:

a wet compartment containing a coupling liquid with an acoustic window, and housing the carrier, and a dry compartment housing electronic equipment, communications capabilities, a power supply unit, and ports for a battery charger and a computer.

18. The ultrasound scanner according to claim 12, wherein the mechanical drive system includes a motion transmission system between the stepper motor and the carrier supporting the transducer element, wherein the motion transmission system includes a toothed belt interlocking with notches on a rotary pinion at a stepper motor outlet and the notches on the rotary pinion at an inlet of the carrier supporting the transducer element.

19. The ultrasound scanner according to claim 16, wherein the portable digital device and the probe are arranged to ensure that:

resources of the portable digital device are used to calculate the angular offset between the emission echo lines and the return echo lines associated with the operation of the mechanical drive system and/or compensation of the angular offset; and/or resources of the probe are used to calculate the angular offset between the emission echo lines and the return echo lines associated with the operation of the mechanical drive system and/or compensation of the angular offset.

* * * * *